& nbsp;

(12) United States Patent
Mythen

(10) Patent No.: US 9,205,213 B2
(45) Date of Patent: Dec. 8, 2015

(54) TUBE PLACEMENT APPARATUS

(75) Inventor: Michael Mythen, London (GB)

(73) Assignee: Smiths Group PLC, London (GB)

( * ) Notice: Subject to any disclaimer, the term of this patent is extended or adjusted under 35 U.S.C. 154(b) by 2567 days.

(21) Appl. No.: 11/885,472

(22) PCT Filed: Mar. 16, 2006

(86) PCT No.: PCT/GB2006/000956
§ 371 (c)(1),
(2), (4) Date: Aug. 31, 2007

(87) PCT Pub. No.: WO2006/100442
PCT Pub. Date: Sep. 28, 2006

(65) Prior Publication Data
US 2008/0168986 A1  Jul. 17, 2008

(30) Foreign Application Priority Data
Mar. 19, 2005 (GB) .................................. 0505723.7

(51) Int. Cl.
*A61M 16/04* (2006.01)
*A61M 25/06* (2006.01)
*A61M 25/00* (2006.01)
*A61B 19/00* (2006.01)

(52) U.S. Cl.
CPC ........... *A61M 16/0472* (2013.01); *A61M 16/04* (2013.01); *A61M 16/0465* (2013.01); *A61M 25/06* (2013.01); *A61B 2019/306* (2013.01); *A61B 2019/5437* (2013.01); *A61M 16/0434* (2013.01); *A61M 16/0488* (2013.01); *A61M 2025/0008* (2013.01); *A61M 2205/583* (2013.01); *A61M 2205/6081* (2013.01)

(58) Field of Classification Search
CPC . A61M 16/00; A61M 16/0488; A61M 16/04; A61M 16/0463; A61M 16/0497; A61M 16/0465; A61M 16/0472; A61M 25/00; A61M 25/06; A61M 2025/0008
USPC ............. 128/200.26, 207.14, 207.15, 207.17, 128/207.29
See application file for complete search history.

(56) References Cited

U.S. PATENT DOCUMENTS

| 3,993,079 | A | * | 11/1976 | Henriques de Gatztanondo ............ 604/164.01 |
| 4,364,391 | A | * | 12/1982 | Toye ........................ 128/207.29 |
| 4,649,913 | A | * | 3/1987 | Watson ..................... 128/207.14 |
| 4,677,978 | A | | 7/1987 | Melker et al. |
| 4,889,112 | A | * | 12/1989 | Schachner et al. ....... 128/200.26 |

(Continued)

FOREIGN PATENT DOCUMENTS

| JP | 3076922 B2 | 8/2000 |
| JP | 204081861 A | 3/2004 |
| WO | WO2005011530 A | 2/2005 |

*Primary Examiner* — Justine Yu
*Assistant Examiner* — Colin W Stuart
(74) *Attorney, Agent, or Firm* — Louis Woo

(57) ABSTRACT

A tracheostomy instrument (1) used for inserting a tracheostomy tube has a needle (10) with colored bands (13) along its length and connected with a syringe (14) at its machine end. The syringe (14) is used to detect when the trachea (3) has been penetrated; the depth of penetration is indicated by observing which colored band (13) aligns with the skin surface (5). The machine end of the tracheostomy tube shaft (20) has a number of colored bands (26) corresponding to the bands (13) on the needle (10). A flange (24) is movable along the tube (2) and is locked in position against the colored band (26) corresponding to the band (13) on the needle (10) aligned with the skin surface (5).

3 Claims, 2 Drawing Sheets

(56) References Cited

U.S. PATENT DOCUMENTS

| | | |
|---|---|---|
| 5,055,107 A | 10/1991 | Lester et al. |
| 5,078,743 A | 1/1992 | Mikalov et al. |
| 5,197,465 A | 3/1993 | Montgomery et al. |
| 5,290,310 A * | 3/1994 | Makower et al. ............. 606/213 |
| 5,343,874 A | 9/1994 | Picha et al. |
| 5,443,064 A | 8/1995 | Theis et al. |
| 5,515,844 A * | 5/1996 | Christopher ............. 128/200.26 |
| 6,200,274 B1 * | 3/2001 | McNeirney ................... 600/562 |
| 6,494,848 B1 * | 12/2002 | Sommercorn et al. ........ 600/587 |
| 6,613,002 B1 * | 9/2003 | Clark et al. ................... 600/593 |
| 6,764,453 B2 * | 7/2004 | Meier ........................... 600/587 |
| 2004/0084051 A1 | 5/2004 | Hipolito et al. |

* cited by examiner

TUBE PLACEMENT APPARATUS

This invention relates to tube placement apparatus of the kind including a tube and an elongate penetration instrument, the instrument being adapted to penetrate a body cavity in which the tube is to be placed.

In various surgical situations it is necessary to make a passage into a body cavity so that a tube can have one end inserted in the cavity. For example, in some tracheostomy procedures, a passage is made initially through neck tissue into the trachea using a hollow needle. The passage is subsequently enlarged using one or more dilators so that a tracheostomy tube can be inserted. In some circumstances, such as where the patient is obese and has an excessive thickness of tissue overlying the trachea, it can be difficult to estimate the thickness of the tissue and conventional tubes with fixed flanges may not be suitable. Often it is preferable to use a tube with a flange that can be moved along the length of the tube shaft so that it can be positioned appropriately according to the patient's build. A problem with such tubes is that the flange has to be manipulated and positioned after the tube has been inserted, which can cause trauma to the patient.

It is an object of the present invention to provide alternative tube placement apparatus and methods.

According to one aspect of the present invention there is provided tube placement apparatus of the above-specified kind, characterised in that the instrument is provided with visible markings along its length by which the extent of insertion of the instrument can be readily ascertained, that the tube is correspondingly provided with visible markings of the same character as those on the instrument, and that the tube has a flange movable and lockable along the length of the tube against the markings so that the flange can be positioned appropriately by observation of the markings on the instrument indicative of extent of penetration.

The visible markings on the instrument and the tube are preferably bands extending around the instrument and tube. The markings are preferably coloured differently from one another. The instrument may include a needle with a cutting tip. The instrument may include a device, such as a syringe, for indicating when the tip of the instrument has penetrated the body cavity. The tube may be a tracheostomy tube and the instrument may be adapted to penetrate the trachea through neck tissue.

According to a second aspect of the present invention there is provided a tube for use in apparatus according to the above one aspect of the invention.

According to a third aspect of the present invention there is provided an instrument for use in apparatus according to the above one aspect of the invention.

According to a fourth aspect of the present invention there is provided a method of placing a tube in a body cavity comprising the steps of: penetrating body tissue with an instrument, detecting when the instrument has penetrated the body cavity, observing markings along the instrument to determine which marking is aligned with the skin surface, displacing a flange along a tube until the flange is aligned with a marking on the tube corresponding to the marking on the instrument, retaining the flange in position on the tube and subsequently inserting the tube along the passage established by the instrument until the flange on the tube comes into contact with the skin surface.

According to a fifth aspect of the present invention there is provided apparatus for use in a method according to the above fourth aspect of the present invention.

Apparatus, and a method, for placing a tracheostomy tube will now be described, by way of example, with reference to the accompanying drawings, in which.

Figure 1:
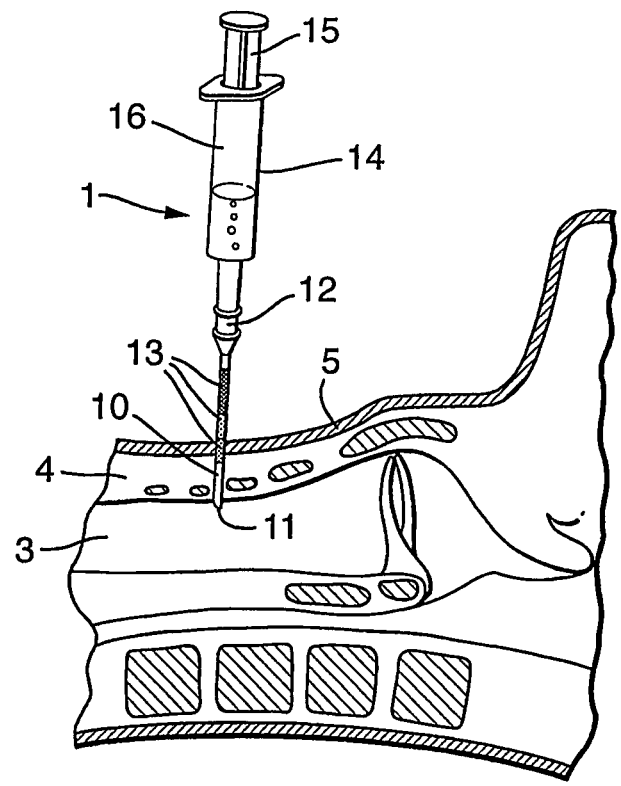
FIG. 1 is a sectional view showing a needle instrument being inserted to the trachea.
Figure 2:
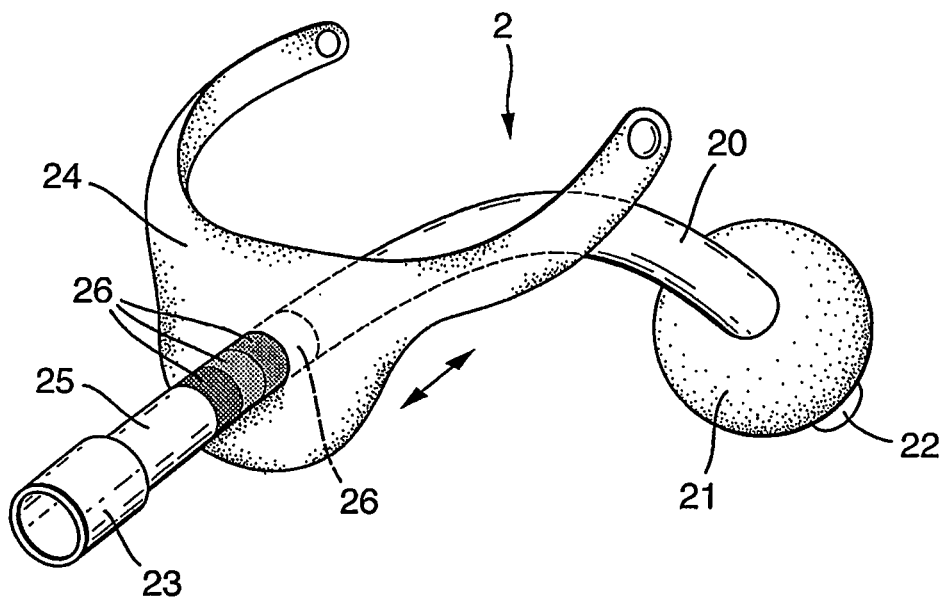
FIG. 2 is a perspective view of the tracheostomy tube.

With reference first to FIGS. 1 and 2, the apparatus comprises a needle instrument 1 and a tracheostomy tube 2.

The needle instrument 1 is used to make the initial penetration of the trachea and comprises a rigid, hollow, steel needle 10 with a cutting tip 11 at its forward end and a hub 12 at its rear end. The needle 10 has visible markings 13 along its length in the form of four, differently coloured bands extending around the circumference of the needle and arranged one after the other. The needle could carry an outer cannula, in which case the markings could be provided on the cannula. It is not essential that the markings be coloured bands since they could be numbers or letters but, given the relatively small diameter of the needle, coloured bands are believed to be the most conspicuous. The bands 13 are located along that part of the length of the needle 10 corresponding to the range of variation in neck tissue thicknesses likely to be met. The instrument 1 also includes a syringe 14 having its nose connected with the hub 12. The syringe 14 is used to detect when the tip 11 of the needle 10 penetrates the trachea 3. It may be used in the loss-of-resistance technique where the user applies light pressure to the syringe plunger 15 while the needle is being inserted through neck tissue 4. Contact of the tip 11 with the neck tissue 4 prevents air escaping, so the plunger 15 does not move relative to the barrel 16. When the tip 11 of the needle 10 clears the tissue 4 on entry to the trachea 3, air can escape and hence allow the plunger 15 to move forwardly, which is immediately apparent to the user. Entry to the trachea 3 can be confirmed by withdrawing the plunger 15 relative to the barrel 16 to ensure that this aspirates air within the trachea. Other forms of instrument could be used to penetrate the trachea, which would be similarly visibly marked.

As soon as the tip 11 enters the trachea 3 the user notes the colour of the band 13 aligned with the surface of the skin 5. The syringe 14 is then disconnected from the hub 12, leaving the needle 10 in position. A guidewire (not shown) is then slid along the bore of the needle 10 so that one end enters the trachea 3. The needle 10 is slid rearwardly out of the patient along the guidewire, which is left in position. Where the needle carries a cannula, the needle would be removed after penetration to leave the cannula in place and the guidewire would be inserted along the cannula. A dilator (not shown), or series of dilators of increasing size, is then slid along the guidewire to enlarge the passage through the neck tissue 4 to a size sufficient to receive the tracheostomy tube 2.

Figure 3:
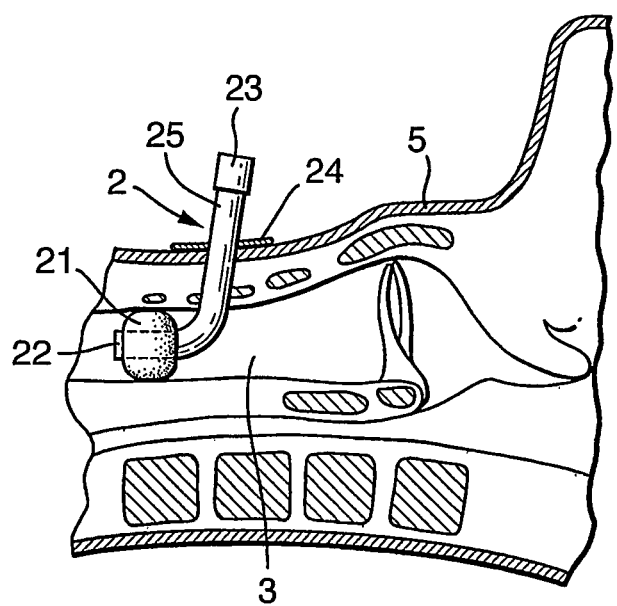
FIG. 3 is a sectional view showing the tube inserted in the trachea.

The tube 2 has a tubular shaft 20 with a sealing balloon 21 close to its forward, patient end 22. Its rear, machine end is provided with a conventional 15 mm coupling 23. The tube 2 also has a neck flange 24 of the kind that is slidable along the shaft 20 and that can be locked in any desired position. The mechanism (not shown) by which the flange 24 is locked in position could be of any conventional kind such as described in, for example, U.S. Pat. No. 5,026,352, U.S. Pat. No. 4,249,529, U.S. Pat. No. 4,449,527, U.S. Pat. No. 4,498,903, U.S. Pat. No. 4,530,354, U.S. Pat. No. 4,530,354, U.S. Pat. No. 4,649,913, U.S. Pat. No. 4,683,882, U.S. Pat. No. 4,774,944, WO80/02645, WO84/03217, U.S. Pat. No. 4,278,081 and GB0503081.2. The rear, machine end of the tube has a straight portion 25, along which the flange 24 can be positioned, and a part of the length of this portion has visible markings of the same character as those on the needle, in the form of a series of four differently coloured bands 26 located one after the other to provide a pattern of bands of the same colour and arranged in the same order as the bands 13 on the needle 10. Before inserting the tube 2, the user positions the flange 24 against the coloured band 26 corresponding to the band 13 on the needle 10 that aligns with the skin surface 5. He then locks the flange 24 in position on the shaft 20. The tube 2 is then inserted in the usual way on an introducer (not shown), which is slid along the guidewire and is subsequently removed to leave the tube in position in the trachea 3 as shown in FIG. 3.

It may be necessary to adjust the position of the flange 24 slightly when the tube 2 has been almost fully inserted in order to accommodate for variations in anatomy. Whilst the needle instrument 1 provides an indication of the thickness of neck tissue 4, it does not give any indication of variations in the size of the trachea, which can affect how far the tube 2 should be inserted. The present arrangement does, however, enable the flange 24 to be prior positioned relatively accurately and reduces the amount of manipulation necessary while the tube is in the patient. This can considerably reduce patient trauma and discomfort.

The present invention is not restricted to tracheostomy tubes but could be used with other tubes placed in the body.

The invention claimed is:

1. A method of placing a tube in a body cavity comprising the steps of:
penetrating body tissue with an instrument, detecting when the instrument has penetrated the body cavity, observing markings along the instrument to determine which marking is aligned with a skin surface, displacing a flange along a tube until the flange is aligned with a marking on the tube corresponding to the marking on the instrument, retaining the flange in position on the tube and subsequently inserting the tube along a passage established by the instrument until the flange on the tube comes into contact with the skin surface.

2. Method according to claim 1, wherein the markings along the instrument comprise bands of different colors, and wherein observing markings along the instrument comprises observing the bands of different colors to determine which band of color is aligned with the skin surface when the instrument has penetrated the body.

3. Method of claim 2, wherein the markings along the tube comprises bands of different colors that correspond to the bands of colors along the instrument, and wherein the flange is displaced along the tube to align with the color band that corresponds to the band of color along the instrument determined to be aligned with the skin surface.

* * * * *